US00PP10795P

United States Patent [19]

Wain

[11] Patent Number: Plant 10,795

[45] Date of Patent: Feb. 16, 1999

[54] CHRYSANTHEMUM PLANT NAMED 'FROSTY TIME'

[75] Inventor: Peter Wain, Portsmouth, United Kingdom

[73] Assignee: Cleangro, Ltd., West Sussex, England

[21] Appl. No.: 838,351

[22] Filed: Apr. 8, 1997

[51] Int. Cl.[6] ..... A01H 5/00

[52] U.S. Cl. ..... Plt./77

[58] Field of Search ..... Plt./77

*Primary Examiner*—Howard J. Locker
*Attorney, Agent, or Firm*—Christie, Parker & Hale, LLP

[57] ABSTRACT

A new plant variety of Chrysanthemum having pure white flowers with green centers.

2 Drawing Sheets

BACKGROUND OF THE INVENTION

The present invention is directed to a new and distinct variety of Chrysanthemum botanically classified as *Dendranthema grandiflora*. The varietal denomination of the new chrysanthemum is 'Frosty Time.'

The female and male parents of the new varieties are undistributed, unpatented seedlings identified as P17-10 and P111-19, respectively. The new variety has been asexually reproduced by vegetative cuttings in Ventura County, Calif. and the distinguishing characteristics are retained through successive generations of asexual reproduction.

SUMMARY OF THE INVENTION

'Frosty Time' is a spray type pot forcing chrysanthemum plant variety producing pure white flowers on plants capable of being grown commercially in a greenhouse.

BRIEF DESCRIPTION OF ILLUSTRATIONS

The accompanying photographs show typical specimens of the new variety with colors being as nearly true as possible with illustrations of this type. One illustration shows 'Frosty Time' grown as a pinched pot mum and the other illustration is a close-up of the flowers.

DESCRIPTION OF THE PLANT

The following description of the new variety is of specimens grown in a greenhouse in Oxnard, Ventura County, Calif. in the month of October. 'Frosty Time' has not been observed under all possible environmental conditions. The phenotype may vary significantly with variations in the environment such as temperature, light intensity, day length and cultural conditions. Color values provided in the description are from The Royal Horticultural Society Colour Charts (R.H.S.C.C.), unless otherwise indicated.

Plants of the new variety has been grown successfully under temperature conditions averaging about 65° F. at night and about 75°–85° F. during the day under light conditions of about 5,000–6,000 foot candles. The plants respond well to use of growth retardant, such as one B-9 treatment at about 2000 ppm. To produce a commercial product the plants may be pinched once with the center bud removed. It has been observed that the shelf life of 'Frosty Time' is about 21 days with the response time of about 8 weeks.

Plant

Habit: Spreading.
Height: About 20 cm after one treatment with growth retardant as described above.
Branching characteristics: Strong brancher.
Number of breaks from pinch: About 3.
Typical container size to be grown in: 4", 5", 6", 8", 10".
Length of lateral branches:
*Average.*—About 18 cm.
Stem color: Near 146B.

Foliage

Leaf arrangement: Alternate.
Number of leaves per lateral Branch: Average leaves per lateral branch about 12, very leafy plant, irregular shapes and sizes.
(1) Size: Length — Average about 8.2 cm. Width — Average about 4.3 cm.
(2) Shape: Ovate; some elliptic.
(3) Attachment: Petioled.
(4) Apex: Obtuse with serration.
(5) Base: Tapered.

| (6) Color: | Mature | Young |
|---|---|---|
| Top: | Near 137A | Near 137A |
| Bottom: | Near 138B | Near 138B |

Margin: Lobed with slight serrations.
Aspect: Flat, curling under upon aging.
Surface characteristics: Top-puberulent; Bottom-puberulent.
Venation: Palmately net, main veins prominent on underside of leaf, main vein coloration near 144B, veinlet coloration is near 138B.
Petiole:
(1) *Length.*—About 2.6 cm.
(2) *Color.*—Near 143c.
(3) *Other characteristics.*—Winged.
Stipule: Not present.

Flower

Inflorescence form: Cymose cluster.
Flower form: Decorative.
Flower shape: Irregular circle.
Flower color (general): Pure white.
Blooms: About 3 blooms per branch.
(1) *Diameter.*—About 11 cm.
(2) *Depth.*—About 1.8 cm.

Sepal:

(1) *Number.*—About 28.

(2) *Color.*—Near 137C.

(3) *General appearance.*—Membranous edged, strap shaped.

Peduncle:

(1) *Length.*—Average about 10.5 cm.

(2) *Habit.*—Upright, very little curving.

(3) *Surface.*—Tomentose.

(4) *Color.*—Near 138B.

(5) *Strength.*—Very strong.

Bud:

(1) *Shape.*—Very flat sphere.

(2) *Diameter.*—Avg. about 1 cm.

(3) *Color.*—Near 144 A.

(4) *Height.*—About 0.5 cm.

Ray florets:

(1) *Number per flower.*—Average about 310.

(2) *Fused.*—Not fused to each other as a group.

(3) *Texture.*—Matte.

(4) *Shape.*—Individual ray florets are tubular at the base and tapered.

(5) *Apex.*—3 irregular lobes.

(6) *Base.*—Tapered, fusing near base.

(7) *Margin.*—Entire.

(8) *Aspect.*—Rippled, curling under, some undulation.

(9) *Length.*—Avg. About 5.1 cm.

(10) *Width.*—Avg. About 1.8 cm. Color — top side: Immature: Near 155 B. Mature: Near 155D. Fading: Near 155D. Color — under side: Immature: Near 155B. Mature: Near 155D. Fading: Near 155D.

Disc florets:

(1) *Number per flower.*—Average about 22.

(2) *Texture.*—Glossy.

(3) *Shape.*—Cylindric.

(4) *Margin.*—Entire.

(5) *Length.*—About 0.3 cm.

(6) *Width.*—About 0.08 cm.

(7) *Fragrance.*—Almost none.

*Color.*—Immature: Near 154D. Mature: Near 154A, tip near 2C middle. Fading: Near 7A.

Description of flower as it ages:

Tips and centers turn brown. Outer petals drop almost straight down. Center remains tight while outer petals are very loose.

Reproductive Organs

Ray florets:

*Pistillate.*—(1) Pistil number: 1 per flower. (2) Ovary Shape: Egg shaped. (3) Stigma shape: 2-forked, curling out irregularly, rarely 3-forked. (4) Stigma color: Near 15C. (5) Style length: About 0.5 cm. (6) Style color: Near 154C.

Disc florets: Pistillate and staminate.

*Pistillate.*—(1) Pistil number: 1 per flower. (2) Stigma shape: linear. (3) Style length: About 0.2 cm, near 154A.

*Staminate.*—(1) Stamen number: About 5. (2) Anther length: About 0.15 cm. (3) Anther shape: linear, translucent yellow. (4) Pollen quantity: None.

What is claimed is:

1. A new and distinct variety of Chrysanthemum plant substantially as herein shown and described.

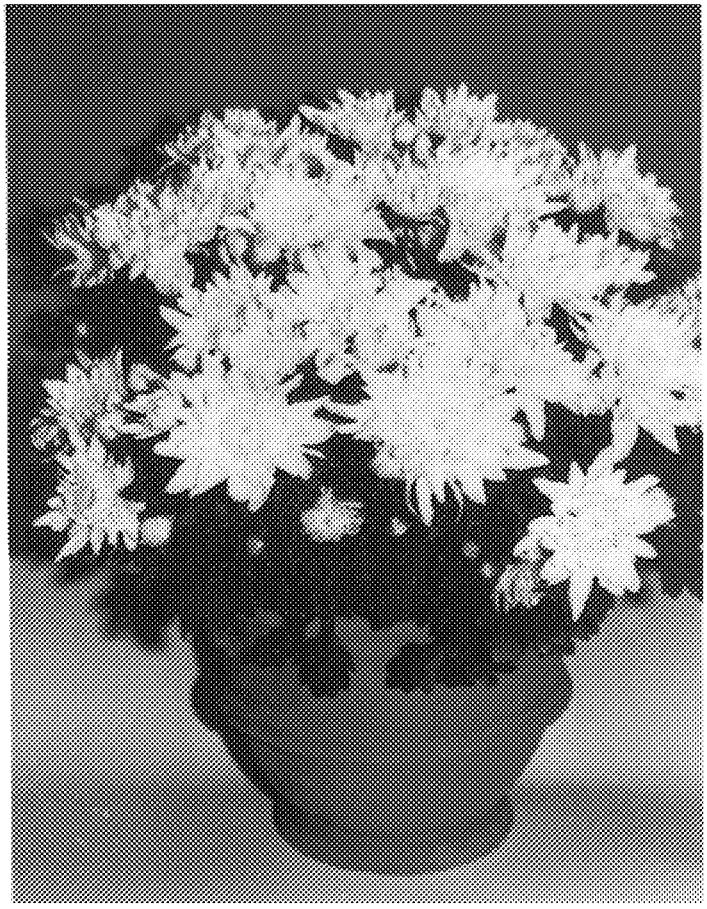

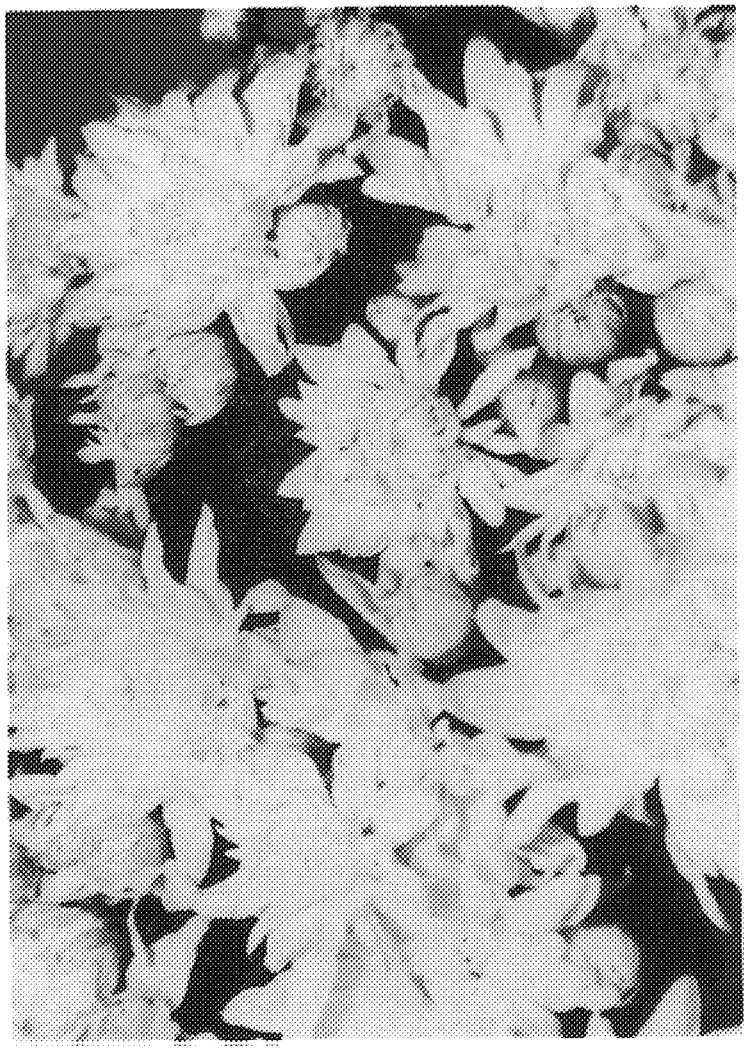

* * * * *